(12) United States Patent
Kane et al.

(10) Patent No.: US 6,217,731 B1
(45) Date of Patent: *Apr. 17, 2001

(54) METHOD AND APPARATUS FOR MONITORING AND DISPLAYING THE STATUS OF A PARALLEL CAPILLARY ELECTROPHORESIS DEVICE

(75) Inventors: Thomas E. Kane; Robert Eugene Fields, III, both of State College, PA (US)

(73) Assignee: Spectrumedix Corporation, State College, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/176,106

(22) Filed: Oct. 21, 1998

(51) Int. Cl.[7] .................................................... G01N 27/26
(52) U.S. Cl. ............................................ 204/451; 204/602
(58) Field of Search .................................. 204/451, 601, 204/602

(56) References Cited

U.S. PATENT DOCUMENTS

| | | | |
|---|---|---|---|
| 5,384,024 | * | 1/1995 | Moring et al. ........................ 204/602 |
| 5,441,613 | * | 8/1995 | McCormick et al. ................ 204/452 |
| 5,858,195 | * | 1/1999 | Ramsey ................................. 204/601 |
| 5,885,430 | * | 3/1999 | Kernan et al. ........................ 204/453 |
| 5,963,456 | * | 3/1999 | Klein et al. ............................. 702/19 |
| 5,965,001 | * | 10/1999 | Chow et al. .......................... 204/600 |

* cited by examiner

*Primary Examiner*—Arlen Soderquist
*Assistant Examiner*—Alex Noguerola
(74) *Attorney, Agent, or Firm*—Pennie & Edmonds LLP (57) ABSTRACT

An automated parallel electrophoresis system including a plurality of capillaries configured to accommodate samples during an electrophoresis run which includes a plurality of phases. The system also includes a control circuit coupled to the capillaries and configured to perform one of monitoring and regulating the capillaries, a display monitor and a computer processor coupled to the control circuit and the display monitor. The computer processor includes a input/output (I/O) interface configured to communicate with the control circuit and a first computer memory storing a display program which displays a graphical user interface on the display monitor. In addition, a method of monitoring and regulating an electrophoresis run performed on a parallel capillary electrophoresis system which comprises a plurality of capillaries configured to accommodate samples during an electrophoresis run. The method includes the steps of making electrical measurements on the capillaries during the electrophoresis run and displaying the measurements on a display screen.

20 Claims, 6 Drawing Sheets

METHOD AND APPARATUS FOR MONITORING AND DISPLAYING THE STATUS OF A PARALLEL CAPILLARY ELECTROPHORESIS DEVICE

FIELD OF INVENTION

This invention relates to an apparatus and method of automated capillary electrophoresis device (CED). More specifically, it relates to a computer automated CED in which a graphical user interface is provided to monitor and display various aspects of the CED.

BACKGROUND

Electrophoresis is a well-known technique for separating macromolecules. In an electrophoretic application, molecules in a sample to be tested are migrated in a medium across which a voltage potential is applied. The sample is propagated through a gel which acts as a sieving matrix to help retard and separate the individual molecules as they migrate. Oftentimes, a capillary tube (hereinafter "capillary") is provided for holding the gel and for allowing the sample to migrate therein.

Figure 1:
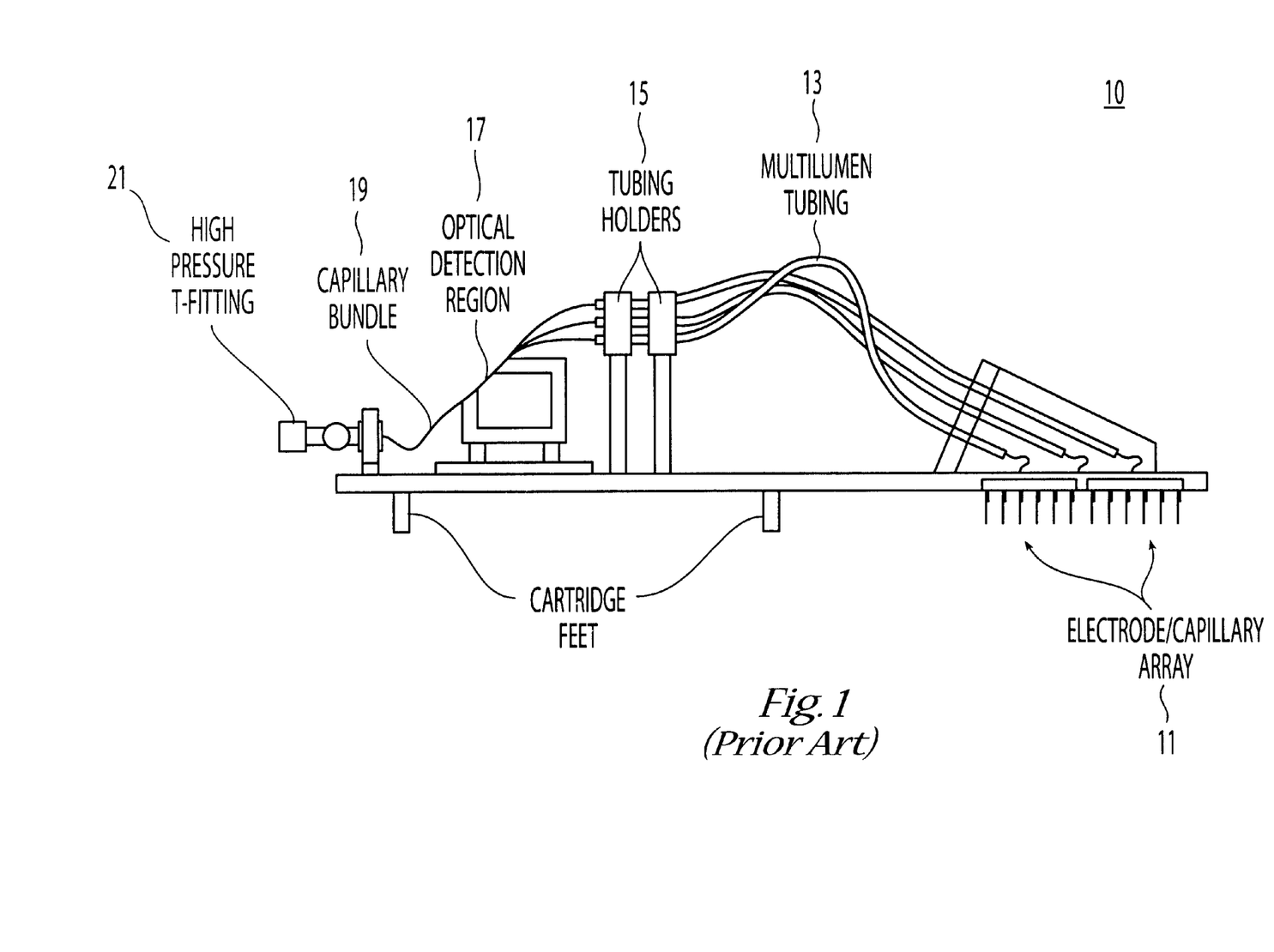
FIG. 1 is a schematic layout of a conventional CED.

A conventional capillary electrophoresis device (CED) 10 provided with a plurality of capillaries is depicted in FIG. 1. The conventional CED 10 includes an electrode/capillary array 11, multilumen tubing 13, tubing holders 15, optical detection region 17, capillary bundle 19 and high pressure T-fitting 21. The capillaries have sample ends disposed in the electrode/capillary array 11 and second ends received by the high pressure T-fitting 21.

The electrode/capillary array 11 includes electrodes and the sample ends of capillaries protruding from the bottom side of the CED. The electrodes and the sample ends of capillaries are arranged to be dipped into corresponding sample wells in a 96-well or a 384-well microtitre tray; this requires 96 or 384 capillaries in order to fully utilized every well on the microtitre tray. (The microtitre tray is not illustrated in FIG. 1.)

The capillaries run inside of corresponding multilumen tubes 15 which are firmly fixed in place by the tubing holders 15. Exposed portions of the capillaries, lined up side-by-side and without the protection of multilumen tubing, then pass through the optical detection region 17, which includes a CCD camera assembly (not shown in FIG. 1). The CCD camera assembly captures images of samples traveling inside the exposed capillaries. The exposed second ends of the capillaries are then bundled together and fitted into the high pressure T-fitting.

The above described conventional CED is utilized to perform electrophoresis runs. An exemplary electrophoresis run may include the steps of: conditioning and preparing the capillaries by washing capillaries by injecting wash solutions to the capillaries and refilling the capillaries with gels; introducing samples to the samples ends of the capillaries when the capillaries are conditioned properly to receive the samples; applying a voltage potential, i.e., 12 KV, between the sample ends of the capillaries and the high pressure T-fitting; and capturing images of the samples as they travel inside capillaries by the CCD camera at the optical detection region. A plurality of valves and pumps are provided to the CED in order to properly carry out the washing, reconditioning and refilling cycles with appropriate liquid solutions.

More detailed description of the above features are described in U.S. patent application Ser. No. 09/105,988, which is incorporated herein in its entirety by reference.

An operator of the conventional CED, however, is required to monitor closely the CED during electrophoresis runs. For instance, liquid containers holding wash solutions to be injected into the capillaries must be checked constantly and replenished when the wash solutions are depleted. During an electrophoresis run the operator is also required to be aware of which cycle the electrophoresis run is performing, because each cycle demands the operator to perform different manual tasks. For example, after the capillaries are conditioned with the gel, the operator is required to check the sample tray and the capillaries before applying the voltage potential. This is because if sample tray is not present or if capillaries are not filled with the gel, then applying the voltage potential to the capillaries may damage the CED.

Moreover, this task of manually checking the capillaries is a laborious task, because a small impurity in the gel inserted into the capillaries or an air bubble in the capillaries can cause damage to the CED, and it may also cause the electrophoresis run to be ruined with an unusable data collection. When the samples are abundant, one unsuccessful run is not a problem; however, when the sample are rare samples then one unsuccessful run is catastrophic. In order to reduce the risk, the operator is required to check the capillaries carefully, which is time consuming and tedious. In view of the above shortcomings, what is needed is a system to automatically and monitor and regulate the CED.

BRIEF SUMMARY OF THE INVENTION

This invention provides a method and apparatus for automatic monitoring and regulating capillary electrophoresis devices. In particular, an automated electrophoresis system in accordance with the present invention comprises a plurality of capillaries configured to accommodate samples during an electrophoresis run which includes a plurality of phases; a control circuit coupled to the capillaries and configured to perform at least one of monitoring and regulating the capillaries; and a display coupled to the control circuit and configured to display corresponding information reflecting one of said monitoring and regulating of the capillaries.

The system is further provided with a computer processor coupled to the control circuit and the display. The computer processor including a input/output (I/O) interface configured to communicate with the control circuit, and a first computer memory storing a display program which displays a graphical user interface on the display. The display could be a display monitor.

In one aspect of the invention, the control circuit includes an electrical circuit configured to make electrical measurements of the capillaries. In addition, the electrical circuit comprises a plurality of resistors coupled to the capillaries, and a plurality of multiplexers configured to select one of the electrical voltages to be measured by an analog/digital converter.

In another aspect of the invention, the I/O interface is further configured to receive the electrical measurements from the control circuit, and the display program is further configured to graphically display the electrical measurements on the display monitor.

The invention is further provided with a capillary malfunction alarm configured to activate an alarm when a malfunction in at least one capillary is detected based on the electrical measurements.

In yet another aspects of the invention, the display program is further configured to continuously display the electrical measurements in real time, to graphically display instantaneous statistical variations of the electrical measurements among the capillaries, or to display a window arranged to interactively allow an operator to select a predetermined number of capillaries whose electrical measurements are to be displayed.

The display program is further configured to display a time line arranged to graphically display an identity and duration of each phase of the electrophoresis run, and an elapsed time indicator which indicates elapsed time from a start of the electrophoresis run, said elapsed time indicator comprising a graphical object which expands along the time line throughout the electrophoresis run.

The present invention is also directed to a method of controlling an electrophoresis run performed on a parallel capillary electrophoresis system which comprises a plurality of capillaries configured to accommodate samples during an electrophoresis run. The method comprises the steps of making electrical measurements of the capillaries to sense electrical conditions during the electrophoresis run and displaying information reflective of the measurements to allow an operator to monitor the electrophoresis run. The electrical measurements are made by measuring voltages across a plurality of resistors that are coupled to the capillaries.

The method further includes the steps of continuously making the electrical measurements during the electrophoresis run and displaying the information reflective of the measurements in real time.

In another aspect of the invention the method further includes the steps of calculating instantaneous averages of the measurements from all the capillaries in real time and activating a capillary malfunction alarm when a measurement from at least one of the capillaries is different by a predetermined amount from the instantaneous average.

In yet another aspect of the invention the method includes the steps of graphically displaying instantaneous statistical variations of the measurements among the capillaries in order to allow the operator to view changes in the electrical conditions of the capillaries in real time, and graphically displaying a two-dimensional grid of graphical objects, each graphical object representing the statistical variation of a corresponding capillary in order to graphically illustrate the changes in the electrical condition of that capillary.

Furthermore, the present invention includes the steps of displaying a time line arranged to graphically display an identity and duration of each phase of the electrophoresis run, and displaying an elapsed time indicator which indicates elapsed time from a start of the electrophoresis run, said elapsed time indicator comprising a graphical object which expands along the time line throughout the electrophoresis run.

DETAILED DESCRIPTION OF THE INVENTION

For the purpose of describing the present invention, the conventional capillary electrophoresis device (CED) described above is utilized; however, it should be noted that automated monitoring and controlling of other similar parallel capillary electrophoresis devices are also contemplated within this invention. The monitoring includes monitoring the conditions of capillaries, gels inserted into the capillaries and samples. The controlling includes controlling various aspects of automatically performing the electrophoresis run, including but not limited to automated control of pumps, valves and a power supply.

Figure 2:
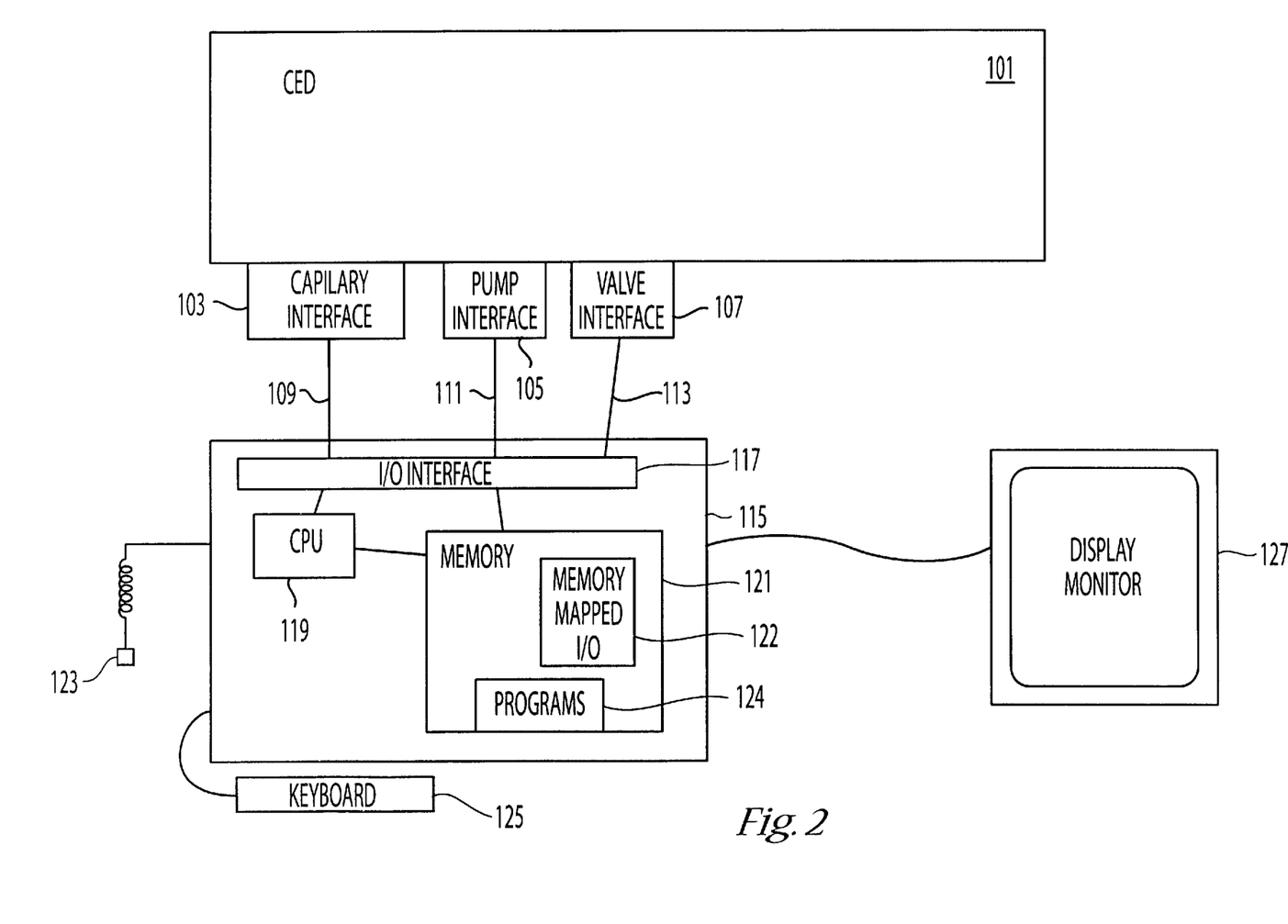
FIG. 2 is an overall block diagram of an automated electrophoresis system.

Referring to FIG. 2, a parallel capillary electrophoresis device is connected to a plurality of interface devices arranged to communicate with a computer processor 115. The interface devices include, preferably, a capillary interface 103, a pump interface 105, and a valve interface 107. These interface devices allow various components of the conventional CED 101 to interface with the computer processor 115 which monitors and controls various aspects of the CED 101.

Figure 3:
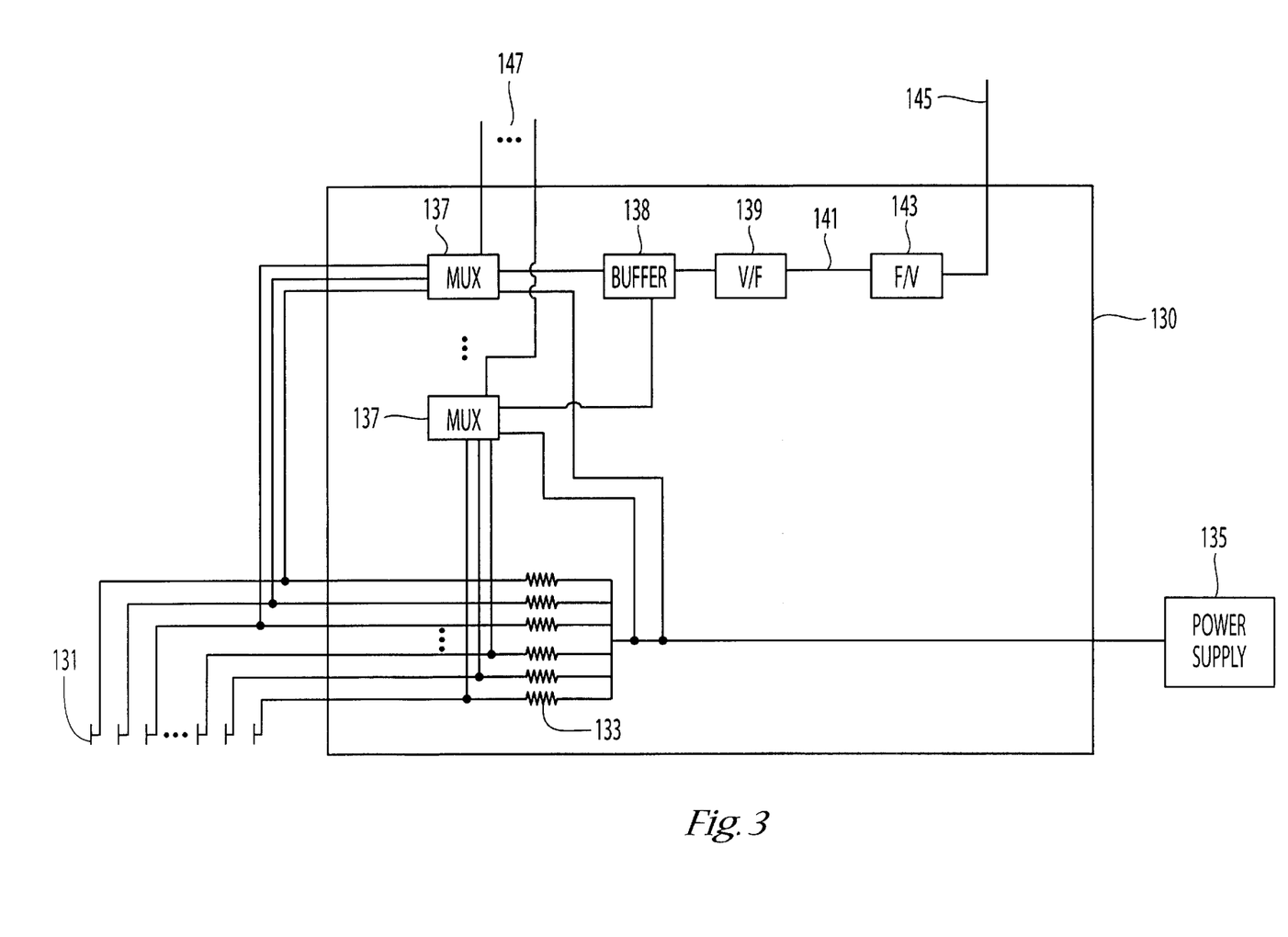
FIG. 3 is a schematic diagram of a current monitoring box.

Referring to FIG. 3, the capillary interface 103 includes a current monitor box 130 configured to make measurements of capillaries. The current monitor box 130 includes electrical wire connections to each of electrodes 131, which are similarly arranged as that of electrodes in the electrode/capillary array 11 of FIG. 1, and a common connection to a power supply 135 which can supply a variable voltage up to 12 KV to the current monitor box 130. In the preferred embodiment, the power supply 135 is controlled by a power supply control box (not shown in FIG. 3). The power supply control box is configured to receive commands from a computer and to control the power supply according to the commands from the computer.

The current monitor box 130 also includes multiplexers 137, voltage sensing resistors 133, a voltage/frequency converter 139, a fiber optic cable 141 and a frequency/voltage converter 143. The current monitor box 130 includes the same number of voltage sensing resistors 133, preferably 12 K ohm each, as that of the electrodes 131. The current monitor box 130 also includes a sufficient number of multiplexers 137 in order to individually address the voltage sensing resistors 133. For instance, for a 96-electrode array, the current monitor box 130 includes 96 voltage sensing resistors and six multiplexers that multiplex 16 lines each.

The multiplexers 137, preferably, ADG 528, manufactured by Analog Device, Inc., are configured to select individually the voltages across the voltage sensing resistors 133. The selected voltage is routed to a buffer amplifier 138 and, then, sent to the voltage/frequency converter 139 where the selected voltage is measured. The buffer 138 is an op-amp, preferably, ADG-648-JN, which provides a high input impedance and a low output impedance. The buffer 138 adds a stable zero-offset or bias to the measurement, so that the voltage/frequency converter 139 is allowed operate at the midpoint of its optimal range when the measured voltage is zero, which results in fast response and accurate measurement. The voltage/frequency converter 139 converts the measured voltage into a pulse train, with its frequency generated based on the measured voltage. The pulse train is converted to an optical signal by an LED fiber optic transmitter. The optical signal is sent over to the frequency/voltage converter 143 via the fiber optical cable 141. The frequency/voltage converter 143 converts the frequency value of the optical signal into an analog signal representing the measured voltage. This analog signal is sent out of the current monitoring box 130 via a communication cable 145. The voltage/frequency converter and the frequency/voltage converter are preferably manufactured by Burr Brown, Inc.

A sufficient number of address bit lines 147 are provided to select which capillary is to be monitored at any given instant using the multiplexers 137. For instance, for 6 by 16 multiplexer configuration discussed above, 7 address bit lines are required (4 address bits to select one from 16, and 3 address bits to select one from 6). In an alternative embodiment, a single fiber cable is provided for the address selection. In this alternative embodiment, the fiber cable allows serial address selection by using 7 address bits as described above or by using an arbitrary number of address bits.

During an electrophoresis run, the voltage from the power supply 135 is applied to the voltage sensing resistors 133, to the electrodes 131, to capillaries and, then, to the high pressure T-fitting (depicted in FIG. 1) which is connected to an electrical ground, thereby establishing an electrical circuit. The current monitoring box is mounted inside a Faraday Cage for protection against high-voltage arcs.

It should be noted that, instead of voltage measurements across the resistors, measurements to the currents flowing through the capillaries or other similarly sensed information of the capillaries can also be used to monitor the capillaries.

Referring back to FIG. 2, the pump interface 105 preferably includes an RS-232 port on each pump. Each of the RS-232 ports on the pumps is connected to a corresponding serial port on the computer processor 115 via an RS-232 cable 111.

The valve interface 107 preferably includes a control port on each valves. Each of the control ports on the valves is connected to a corresponding input/output I/O port on the computer processor 115 via a cable 113.

A current monitor cable 109, which connects the capillary interface 103 and the computer processor 115, includes the address bit lines 147 and the communication cable 145 depicted in FIG. 3.

A control circuit monitors, regulates and otherwise controls the capillaries during electrophoresis runs by using a combination of the capillary interface 103, the pump interface 105, the valve interface 107, an interface to the power supply control box and other equivalent interfaces. The control circuit is coupled to capillaries and a display that displays corresponding information relating to the monitoring or regulating functions of the control circuit. In one embodiment, the display includes a plurality of LEDs with which to represent the monitoring information from the control circuit. In another embodiment, the display includes a display monitor and a computer, which will be described in detail below. It should be noted that the term coupled should be understood as connection between two components by physical electrical cables, wires, wireless communication links, optical and electromagnetic connections or other similar known connections.

The computer processor 115 includes an I/O interface 117, which includes a plurality of serial digital and parallel I/O ports, a CPU 119 and a memory 121. The computer processor 115 is also connected to a display monitor 127, a key board 125 and a mouse 123. The computer processor 115 is preferably a PC manufactured by Dell. It should be noted that one skilled in the art should be able to use a MacIntosh or a UNIX workstation as well with only minor modifications.

The I/O interface 117 includes a plurality of electronic circuit boards for interfacing with various I/O ports. The I/O interface 117 preferably includes a CIO-DAS 08 and a CIO-DO 48H interface boards manufactured by Computer Boards, Inc. The CIO-DAS 08 board includes 8 channels for analog/digital conventions and 24 bit input/output data connections. The CIO-DO 48H board includes 48 output data connections.

The computer memory 121 includes sufficient memory space to store a plurality of computer programs 124 and a memory mapped I/O 122. The computer programs include a regulating program and display program. These programs are retrieved from the memory to the CPU to be executed.

The regulating program controls the multiplexers 137 in the current monitoring box 130, the valves and pumps by writing appropriate commands to the memory map I/O. The following is a list of exemplary tasks carried out by the program:

(a) For selecting one capillary in order to measure the voltage across its voltage sensing register 133, the program writes a number having seven (7) addressing bits into a capillary select address location in the memory map I/O. The capillary select address is then read by the I/O interface 117 which sends it across the address lines 147.

(b) For setting a pump operation level, the program writes a number representing the desired pumping rate level into a pumping rate location in the memory map I/O. In turn, the pumping rate is read out by the I/O interface 117 which sends it across the RS-232 cable 111 over to the pump interface 105.

(c) For opening or closing a valve, the program writes on/off signals to a valve control location in the memory map I/O. The on/off signal is read by the I/O interface board which sends it across the communication cable 113 to the valve interface 107.

Figure 6:
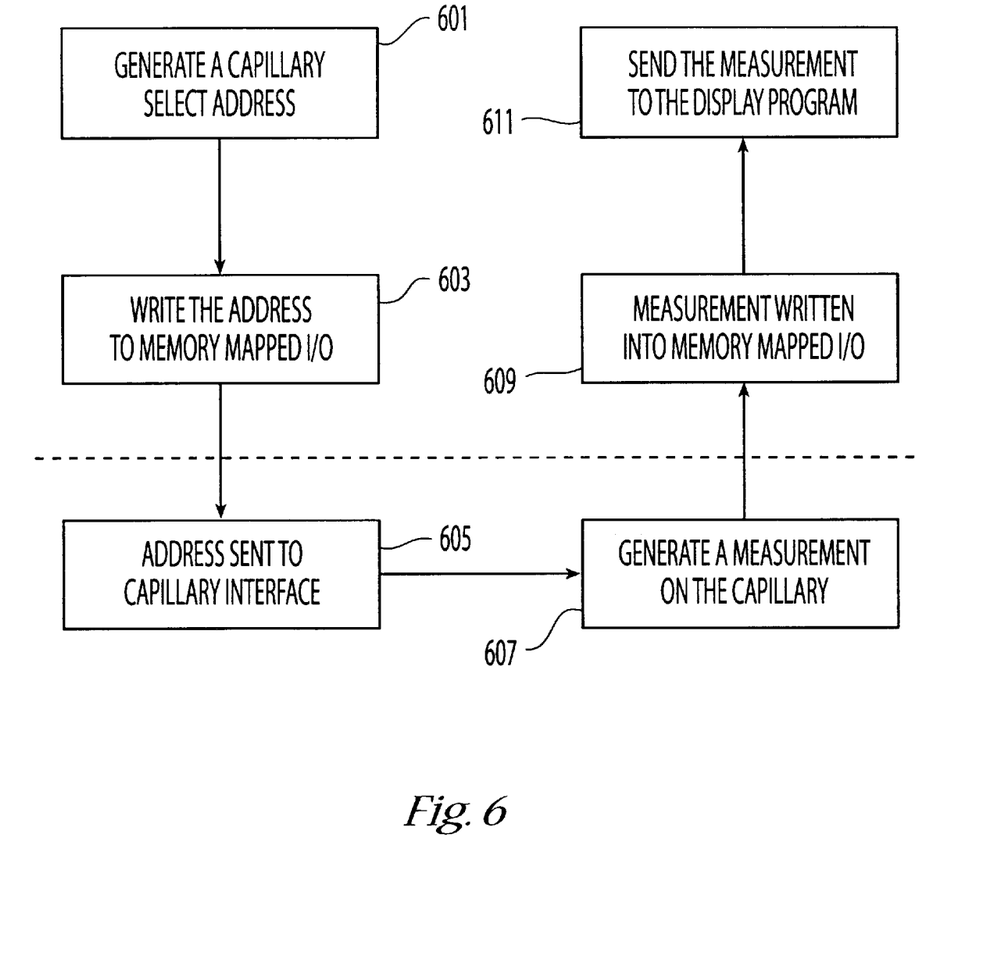
FIG. 6 is a flow chart of an automated method of making electrical measurements of the capillary.

Referring to FIG. 6, the programs execute the steps of the generating a capillary select address 601, writing the address to the memory mapped I/O 603, sending the address to the 605, generating a measurement of addressed capillary 607, writing the measurement into the memory mapped I/O 609, and sending the measurement to the display program 611. Preferably, these steps are continuously repeated during the electrophoresis run for monitoring the capillaries in real time and for accumulating the measurements of the capillaries.

The above steps are performed by various programs and interfaces described above. For instance, the steps of generating the capillary select address and writing the address to the memory mapped I/O are completed by the program; the step of sending the address to the capillary address are performed by the I/O interface; the step of generating the measurement is performed by the capillary interface; the step of writing the measurement into the memory map is performed by the I/O interface; and the step of sending the measurement to the display program is performed by the program.

The display program includes a user interface program for providing an overall graphical user interface of an electrophoresis run to allow the operator to monitor the electrophoresis run based on the collected data by the status collector. The graphical user interface is an interactive graphical interface which displays graphical information on the display monitor 127 and allows the operator to enter commands and other parameters to control the electrophoresis run.

The user interface program is, preferably, implemented by utilizing Lab View® programming language developed by National Instruments, Inc. However, any programming package that includes programming instructions to develop a graphical user interface is sufficient for the purposes of this invention.

The user interface program, when executed, displays a number of window panels on the display monitor 127 designed to communicate specific information with the operator.

Figure 4:
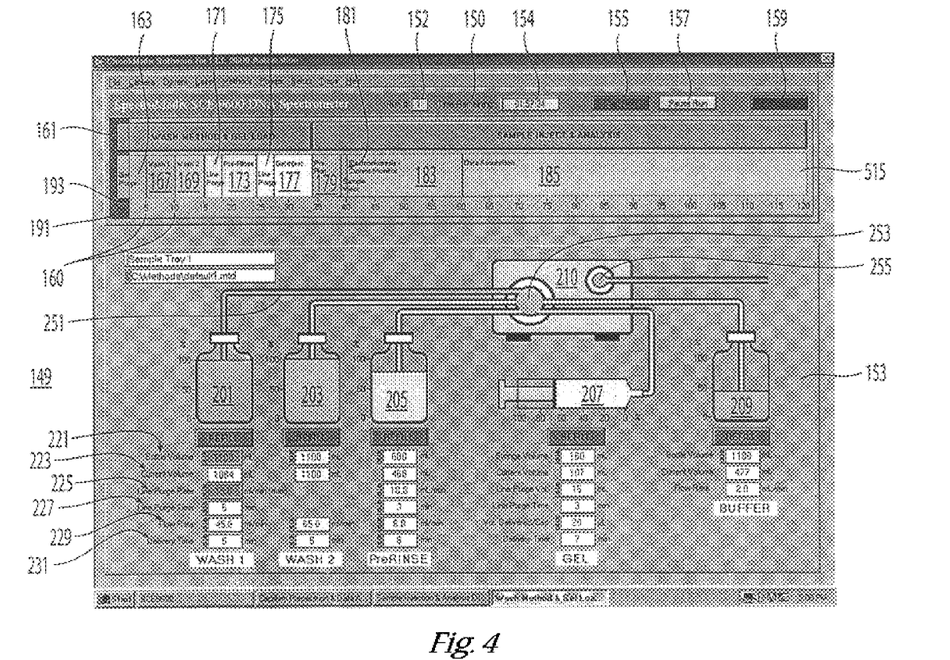
FIG. 4 is a layout of a capillary preparation window and a time line window.

A first user interface window panel 150 illustrated in FIG. 4 includes a general frame window 150, a time line window 151 and a capillary preparation window 153. In an alternative embodiment, each of the time line and the capillary preparation windows form separate window panels rather than forming one window panel as illustrated in FIG. 4.

The general frame window 150 includes a run number display field 152, a time remaining display field 154, a start run option 155, a pause run option 157, and system halt option 159. The run number display field 152 displays the number of runs performed. The time remaining display field 154 displays the remaining clock time of a particular run. The start run option 155 initiates an electrophoresis run. The pause option 157 temporarily stops a run. Finally, the halt option 159 allows the operator to completely stop a run. Each of these options may involve a second window asking for confirmation.

The time line window 151, in turn, includes a plurality of phase blocks designating various stages of an electrophoresis run, a set of numbers designating actual clock elapsed time 160 from the start of a run, and a elapsed time indicator 161.

The phase blocks represent each of the steps necessary to perform an electrophoresis run by identifying each phases with names and the duration of each phases. The time line window depicted in FIG. 3 includes a gel purge 163, first wash 167, second wash 169, first line purge 171, pre-rinse 173, second line purge 175, gel inject 177, pre-run 179, sample inject 181, electrophoresis current monitor 183 and data acquisition phase blocks 185.

During the gel purge phase, the gel inserted into the capillaries in a preceding electrophoresis run is purged from the capillaries. Wash solutions are inserted into the capillaries in the first wash and second wash phases in order to remove any residue of contaminants in the capillaries. The capillaries and various valves are purged in the first line purge phase, rinsed during the pre-rinse phase and purged again during the second line purge phase. New gel is injected into the capillaries during the gel inject phase. This completes the capillary preparation.

The samples are introduced to the capillaries, the electrical currents flowing through the capillaries are checked, and the data are acquired in the remaining phases. The specific number of phases and sequence of their executions are illustrated here only as one specific example of an electrophoresis run for a conventional CED. It should be understood that another CED may use a different number of phases or different sequences of phases. In such case, the time line window is changed to accommodate the changes.

During an electrophoresis run, the elapsed time indicator 161 moves from its starting position at the left hand side of the time line window 151, to the end position the right hand side of the time line window 151. By observing the elapsed time indicator, the operator ascertains the status of the electrophoresis run. The elapsed time indicator preferably includes a shaded frame 191 which surrounds the phase blocks that have been performed and are being performed, and an indicator line 193 at the right-most boundary of the frame 191 expanding to indicate precisely the elapsed time and the current phase. The indicator line 193 illustrated in FIG. 4 indicates that the depicted electrophoresis run is in the gel purge phase 163.

Equivalently, the time line window 151 can be depicted by circular pie chart in which each slice of pie represents a phase block. In such an embodiment, an arm similar to that of a clock arm is utilized to indicate the progress of the electrophoresis run.

In another aspect of the time line window 151, between the phase blocks the computer processor sends appropriate signals to the valves and pumps in order to control the electrophoresis run. For instance, after the gel purge step and before the wash phase, a valve that was opened to allow the gel to be purged needs to be closed, and, during the first wash phase, a pump that injects first wash phase liquid solution into the capillaries needs to be turned on. These tasks are controlled by the regulating program, and are invoked by the display program to write a command, such as open/close commands to a valve or on/off commands to a pump, to an appropriate location in a memory map I/O. As discussed above, the specific location of the memory map I/O is read by the I/O interface 117, and the command written in the memory map I/O is sent to the valve or the pump depending upon the location at which the command was written in the memory map I/O.

The capillary preparation window 153 includes a plurality of graphical objects depicting liquid containers representing liquid solvents required in various stages of an electrophoresis run. In the preferred embodiment, an electrophoresis run requires solvents for the first and second wash phases for cleaning the capillaries, pre-rinse solvents for rinsing the capillaries subsequent to the wash phases, gel for refilling the capillaries, and a buffer solution.

Each of the liquid containers for the solvents 201–205, gel 207 and buffer 209 is depicted by a graphical object. Below each graphically depicted liquid container, data entry fields are provided to enter relevant parameters of a corresponding liquid container.

The relevant parameters of the first wash phase liquid container 201 includes its bottle volume 221, current volume 223, line purge rate 225, line purge time 227, flow rate 229, delivery time 231. The parameters are, preferably, entered manually.

In an alternative embodiment, a liquid container interface is provided, which includes a mechanism to detect the amount of liquids present in each of liquid containers. The mechanism includes a floating magnet inside each of the liquid containers and a corresponding magnet location detector outside of the containers. The magnet location detector are arranged to accurately monitor the position of the floating magnets to the computer. In another alternative embodiment, optical sensors or ultrasonic range finders which detect the presence or absence of the liquids in the containers are provided. In yet another alternative embodiment, a scale is provided to measure the weights of the containers to thereby calculate the remaining liquids in the containers. In these alternative embodiments, the liquid container parameters can be automatically updated based on the information collected by the liquid container interface.

In the first user interface panel 149, the delivery time parameter 231 causes the actual clock time representation to change in the time line window 151. More specifically, in FIG. 4, the delivery time parameter is entered as 5 min, and this is reflected in the time line as 5 min required to run the first wash phase 167. Should the delivery time parameter change to 10 minutes, the actual clock time representation for the first wash phase will be lengthened to 10 minutes and the other phase blocks will shift 5 additional minutes to the right and normalized to a new total time, on the time line window 151. In other words, the time line changes in accordance with the parameter entered in the delivery time parameter field in the capillary preparation window 153.

The second wash 203, the pre-rinse 205, the gel 207 and the buffer 209 liquid containers also include similar parameter fields with similar capabilities as that of the parameter fields of the first wash phase.

The graphical objects representing liquids in each of the liquid bottles are color coded. For example, the first wash liquid container 201 is color coded with blue, the second wash liquid container 203 with pink, the pre-rinse container 205 with green, the gel container 207 with yellow and the buffer container 209 with pink. In the preferred embodiment, each respective colors of the liquid containers flow to a pump graphical object 210 when the corresponding phase is active. The pump graphical object 210 may also include a numerical display of pump rate. In other words, when the first wash phase is active, a graphical conduit 251 connecting the first wash liquid container 201 and pump 218 is filled with green color, and its manifold and delivery areas 253, 255 are filled with green. Similar graphical representation of the other phases are also provided in this invention. The manifold and delivery areas 253, 255 are colored white when there is no pumping.

Figure 5:
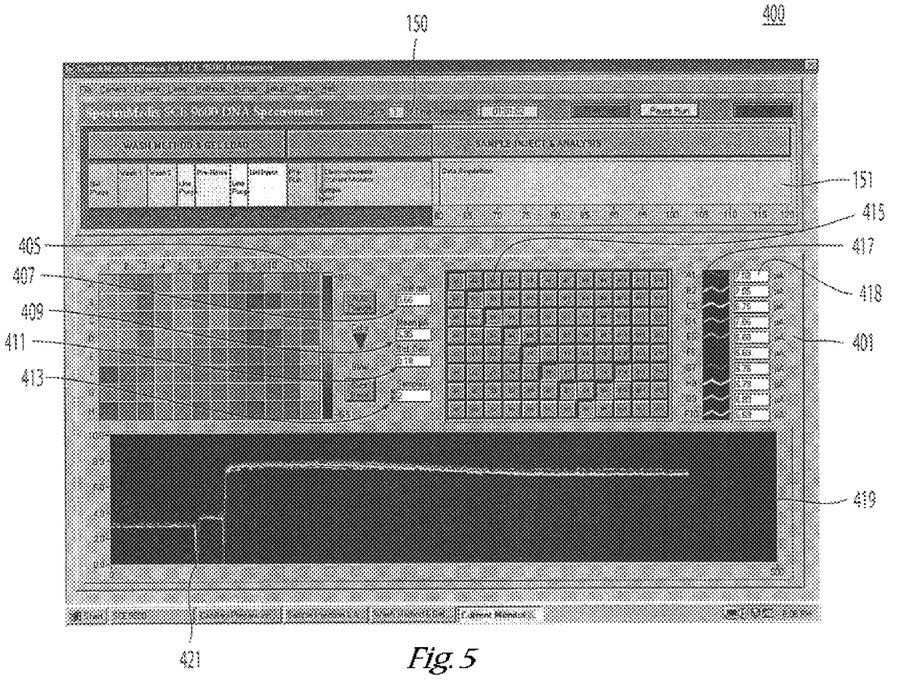
FIG. 5 is a view of a capillary time/current profile window.

Referring to FIG. 5, a second window panel 400 includes, in addition to the general frame window 150 and the time line window 151, a capillary monitor window 401. The capillary monitor window 401 includes a capillary monitoring window 405, a capillary trace window 419, statistical parameter display fields, a capillary selection window 415, a legend field 417 and measured current display field 418. These window can be designed to monitor any type of measurements of the capillaries, such as voltages and currents. In the preferred embodiment, the currents of the capillaries are monitored. The steps of making current measurements of the capillaries are discussed above in connection with the memory mapped I/O.

The capillary monitoring window 405 includes a two dimensional array of color coded boxes corresponding to each of the capillaries. In the preferred embodiment, the capillary monitoring window 405 has 96 boxes, each representing one of the 96 capillaries. The color of each box represents the variation of the measured currents in its corresponding capillary in comparison to an average of measured currents from all the capillaries. This average value is updated on a regular interval, preferably, each time a measurement is made from all of the capillaries.

When the measurements are all near the average values, then each button representing the capillaries are shown as one color, e.g., green. As measurements from some of the capillaries become different from the average value, the colors of those capillaries change. For instance, as the difference between the measurements from one capillary becomes different from the average by more than 2 or 3 standard deviations, the color of the box representing that capillary changes from green to another color, e.g., red. When the difference increases, the hue of red color increases proportionally. In an alternative embodiment, the color can change again to a different color when the difference becomes greater than 4 standard deviations or more.

In this way, the current variation field 405 graphically notifies the operator of any capillary that conducts electrical current that is excessively different from the average value, indicating a potential malfunction in the capillary.

The statistical parameter fields include a total current display field 407, a mean current display field 409, a standard deviation display field 409, and a number of samples field 413. The total current display field 407 displays an estimated total current flowing through the capillaries. The mean current display field 409 displays an average measured currents. The standard deviation display field 409 displays the standard deviation of the measure current values. Finally, the number of samples field 413, which can be modified by the operator, displays the number of samples required to calculate a measured current. In other words, if 2 is designated in the number of samples field 413, two current readings from a capillary value and are averaged and that average value is assigned in that capillary's instantaneous current.

The capillary selection window 415 includes a two dimensional array of boxes corresponding to each of the capillaries. In the preferred embodiment, up to ten capillaries can be selected. However, in an alternative embodiment, an arbitrary number of capillaries can be selected. The measured currents from these selected capillaries are then displayed in the measured current display field 418. Each selected capillaries are also allocated with a legend in accordance with the legends displayed in the legend field 417.

The capillary trace window 419 graphically superimposes current traces of measured currents 421. In the preferred embodiment, the capillary trace window 419 traces up to ten selected capillaries in accordance with the selection made by the operator using the capillary selection window 415. Each trace is designated with corresponding legend displayed in the legend field.

When the colors of boxes in the current deviation field 405 turns from green to red, then the user can optionally select the boxes representing corresponding capillaries in the capillary selection field 415. When the boxes are selected, the current traces of the measured currents of the selected capillaries are displayed in the capillary trace window 419.

Even though current traces of only up to ten capillaries are traced in the capillary trace window 419 in the preferred embodiment, currents from all of the capillaries are processed, collected and stored. If desired, current traces from all of the capillaries can be displayed in the capillary trace window 419.

The tracing of the capillaries begins preferably at the pre-run phase 179. The left end of the current traces 421 represent the current measurements made at the beginning of the pre-run phase. The right end of the current traces 421 represent the latest current measurement. For the example illustrated in FIG. 5, the active phase is the current monitoring phase 183. The two dips in the current traces 421 are the measurement made when the phases changed from the pre-run to the sample inject and from the sample inject to the current monitoring phases. The capillaries are, preferably, monitored only during the pre-run, sample inject, and current monitoring phases. In an alternative embodiment, the capillaries can be monitored during the data acquisition phase as well.

During the data acquisition phase, the voltage potential applied to the capillaries is 12 KV. The voltage potential applied to the capillaries during the pre-run, sample injection, and the current monitoring phases, is preferably lower than 12 KV, and, more preferably, between 5–7 KV.

In an alternative embodiment, a capillary malfunction alarm is provided in the status display program. The capillary malfunction alarm is configured to monitor measured currents from all of the capillaries. If one of the measured currents deviate more then a predetermined standard deviation, i.e., 3 standard deviations or more, from the average, the capillary malfunction alarm will notify the operator by activating an alarm.

The alarm is an audible alarm which includes a buzzer driven by the computer processor 115. The alarm also can be an audio program which drives a speaker. The alarm can also be a visual alarm which includes a computer display window displaying a warning message or a flashing light.

While the above invention has been described with reference to certain preferred embodiments, the scope of the present invention is not limited to these embodiments. For instance, the capillary interface device can be designed to measure currents flowing through the capillaries instead of measuring voltages across the voltage sensing resistors; various computer programs discussed above can be parts of a large computer program; and the present invention also can be implemented to accommodate a 384 capillary electrophoresis device or the like. One skilled in the art may find variations of these preferred embodiments which, nevertheless, fall within the spirit of the present invention, whose scope is defined by the claims set forth below.

What is claimed is:

1. An automated parallel electrophoresis system comprising:
    a plurality of capillaries configured to simultaneously accommodate samples during an electrophoresis run which includes a plurality of phases;
    a control circuit configured to monitor an electrical condition of each of the capillaries, the control circuit including an electrical circuit configured to make individual electrical measurements of each of the capillaries; and
    display coupled to the control circuit and configured to display information reflective of the individual electrical measurements.

2. The system according to claim 1, wherein the electrical circuit comprises:
    a plurality of resistors coupled to the capillaries, each capillary being associated with a resistor; and
    at least one multiplexer configured to select a particular one of the resistors for measurement of a voltage drop across that resistor.

3. An automated parallel electrophoresis, system comprising
    a plurality of capillaries configured to simultaneously accommodate samples during an electrophoresis run which includes a plurality of phases;
    a control circuit coupled to the capillaries;
    a display monitor coupled to the control circuit and configured to display information about the electrophoresis run; and
    a computer coupled to the control circuit and the display monitor, the computer including:
    an input/output (I/O) interface configured to communicate with the control circuit; and
    a first computer memory storing a display program which displays a graphical user interface on the display monitor, the graphical user interface configured to permit a user to interactively monitor or regulate at least an electrical condition of each capillary.

4. The system according to claim 3, wherein
    the I/O interface is further configured to receive electrical measurements of the capillaries from the control circuit; and
    the display program is further configured to graphically display the electrical measurements on the display monitor.

5. The system according to claim 4, further comprising:
    a capillary malfunction alarm configured to activate an alarm when a malfunction in at least one capillary is detected based on the electrical measurements.

6. The system according to claim 4, wherein the display program is further configured to continuously display the electrical measurements in real time.

7. The system according to claim 4, wherein the display program is further configured to graphically display statistical variations of the electrical measurements among the capillaries in real time.

8. The system according to claim 4, wherein the display program is further configured display:
    a window arranged to interactively allow an operator to select a predetermined number of capillaries whose electrical measurements are to be displayed in real time.

9. The system according to claim 3, wherein the display program is configured to display:
    a time line arranged to graphically display an identity and duration of each phase of the electrophoresis run.

10. The system according to claim 9, wherein the display program is further configured to display:
    an elapsed time indicator which indicates elapsed time from a start of the electrophoresis run, said elapsed time indicator comprising a graphical object which expands along the time line throughout the electrophoresis run.

11. A method of controlling an electrophoresis run performed on a parallel capillary electrophoresis system which comprises a plurality of capillaries configured to simultaneously accommodate samples during an electrophoresis run which includes a plurality of phases, the method comprising:
    making individual electrical measurements of each of the capillaries to sense electrical conditions during the electrophoresis run;
    displaying information reflective of the electrical measurements to allow an operator to monitor the electrophoresis run; and
    accepting an input to thereby monitor or regulate at least one phase of the electrophoresis run.

12. The method according to claim 11, wherein the electrical measurements are made by measuring voltages across a plurality of resistors that are coupled to the capillaries.

13. The method according to claim 11, which further comprises continuously making the electrical measurements during the electrophoresis run; and displaying the information reflective of the measurements in real time.

14. The method according to claim 13, which further comprises calculating instantaneous averages of the measurements from all the capillaries in real time.

15. The method according to claim 14, which further comprises activating a capillary malfunction alarm when a measurement from at least one of the capillaries is different by a predetermined amount from the instantaneous average.

16. The met to claim 13, which further comprises graphically displaying instantaneous statistical variations of the electrical measurements among the capillaries in order to allow the operator to view changes in the electrical conditions of the capillaries in real time.

17. The method according to claim 16, which further comprises graphically displaying a two-dimensional grid of graphical objects, each graphical object representing the statistical variation of a corresponding capillary in order to graphically illustrate the changes in the electrical condition of that capillary.

18. The method according to claim 13, which further comprises displaying a window arranged to interactively allow an operator to select a predetermined number of capillaries whose electrical measurements are to be displayed in order to monitor a subset of the capillaries.

19. The method according to claim 11, which further comprises displaying a time line arranged to graphically display an identity and duration of each phase of the electrophoresis run in order to graphically illustrate the phases of the electrophoresis run to the operator.

20. The method according to claim 19, which further comprises displaying an elapsed time indicator which indicates elapsed time from a start of the electrophoresis run, said elapsed time indicator comprising a graphical object which expands along the time line throughout the electrophoresis run in order to graphically illustrate the elapsed time to the operator.

* * * * *